United States Patent
Morrison et al.

(10) Patent No.: US 7,147,651 B2
(45) Date of Patent: Dec. 12, 2006

(54) STIFF TIPPED SUTURE

(75) Inventors: David S. Morrison, Long Beach, CA (US); Randall L. Hacker, Naples, FL (US)

(73) Assignee: Arthrex, Inc., Naples, FL (US)

( * ) Notice: Subject to any disclaimer, the term of this patent is extended or adjusted under 35 U.S.C. 154(b) by 582 days.

(21) Appl. No.: 10/359,235

(22) Filed: Feb. 6, 2003

(65) Prior Publication Data
US 2003/0153948 A1    Aug. 14, 2003

Related U.S. Application Data

(60) Provisional application No. 60/354,501, filed on Feb. 8, 2002.

(51) Int. Cl.
A61B 17/04    (2006.01)
A61B 19/00    (2006.01)

(52) U.S. Cl. .................. 606/228; 606/148; 128/898

(58) Field of Classification Search ........ 606/228–231, 606/144, 148, 139, 222–225, 227
See application file for complete search history.

(56) References Cited

U.S. PATENT DOCUMENTS

| | | | |
|---|---|---|---|
| 3,942,532 A | 3/1976 | Hunter et al. | |
| 4,047,533 A | 9/1977 | Perciaccante et al. | |
| 4,103,690 A * | 8/1978 | Harris | 606/144 |
| 4,344,908 A | 8/1982 | Smith et al. | |
| 4,411,854 A | 10/1983 | Maurer et al. | |
| 4,422,993 A | 12/1983 | Smith et al. | |
| 4,430,383 A | 2/1984 | Smith et al. | |
| 4,436,689 A | 3/1984 | Smith et al. | |
| 4,668,717 A | 5/1987 | Lemstra et al. | |
| 4,669,473 A * | 6/1987 | Richards et al. | 606/232 |
| 5,019,093 A | 5/1991 | Kaplan et al. | |
| 5,067,538 A | 11/1991 | Nelson et al. | |
| 5,156,615 A * | 10/1992 | Korthoff et al. | 606/224 |
| 5,234,764 A | 8/1993 | Nelson et al. | |
| 5,261,886 A | 11/1993 | Chesterfield et al. | |
| 5,318,575 A | 6/1994 | Chesterfield et al. | |
| 5,368,595 A * | 11/1994 | Lewis | 606/228 |
| 5,383,925 A | 1/1995 | Schmitt | |
| 5,403,659 A | 4/1995 | Nelson et al. | |
| 5,540,703 A | 7/1996 | Barker, Jr. et al. | |
| 5,562,684 A * | 10/1996 | Kammerer | 606/139 |
| 5,569,302 A | 10/1996 | Proto et al. | |
| 5,630,976 A | 5/1997 | Nelson et al. | |
| 5,720,765 A | 2/1998 | Thal | |
| 6,045,571 A | 4/2000 | Hill et al. | |
| 6,063,105 A | 5/2000 | Totakura | |
| 6,679,895 B1 * | 1/2004 | Sancoff et al. | 606/144 |
| 2004/0010286 A1 * | 1/2004 | Gieringer | 606/228 |

FOREIGN PATENT DOCUMENTS

EP    0561108 A2    9/1993

* cited by examiner

*Primary Examiner*—Julian W. Woo
(74) *Attorney, Agent, or Firm*—Dickstein Shapiro LLP

(57) ABSTRACT

A multi-stranded suture having a stiff portion adjacent to at least one end of the suture to facilitate advancement of the suture through a cannulated surgical suturing instrument. The suture preferably has a non-stiff distal tip to provide flexibility for passing the suture through bends in the surgical instrument.

4 Claims, 2 Drawing Sheets

STIFF TIPPED SUTURE

This application claims the benefit of U.S. Provisional Application Ser. No. 60/354,501, filed Feb. 8, 2002, the entire disclosure of which is incorporated herein by reference.

FIELD OF THE INVENTION

The present invention relates to surgical sutures and, more specifically, to a stiff tipped surgical suture employed in connection with cannulated surgical instruments for passing suture.

BACKGROUND OF THE INVENTION

Both open and endoscopic surgical procedures often require sutures to ligate, join or otherwise treat tissue. Generally, suture needles with attached suture strands are grasped either manually or by forceps and passed through the desired work site so a knot can be tied. While the procedures are fairly uncomplicated in open surgery where most suture sites are readily accessible, in endoscopic procedures, where access to the work site is not readily available, the surgeon must use auxiliary devices to be able to grasp the suture strands and pass them through desired tissue.

Various instruments and techniques have been developed for surgical repairs requiring the passing of sutures to distant locations. For example, one device for advancing suture directly to a work site is described in U.S. Pat. No. 4,890,615 (Caspari et al.), according to which a suture strand is advanced using a roller mechanism to feed the suture through a hollow needle at the end of an elongated tube into the tissue to be sutured. While suitable for mono-filament suture, such roller-type devices may unravel and disentangle multi-stranded suture which is desirable for certain applications.

In addition, since the work site is typically accessible through a small portal or cannula, it is difficult for the surgeon to pass suture through selected tissue and to form a surgical knot into position adjacent the desired tissue to be sutured. Formation of the knot requires the surgeon to manually tie a knot on the suture strands after the suture is threaded through the tissue to be sutured. The suture must be flexible enough to be manipulated and tied by the surgeon, while also being sufficiently stiff to be directed into the desired position. The knot tying operation is often tedious because, while surgical sutures are often coated to improve tactile smoothness, the coated suture reduces the knot integrity. As a result of these setbacks, there is a need for a multi-stranded suture which can be easily advanced through a cannulated surgical instrument to and from a work site.

SUMMARY OF THE INVENTION

The present invention provides a multi-stranded suture comprising a length of suture provided with a stiff portion adjacent at least one end of the suture to facilitate insertion of the suture through the cannulation of a surgical instrument. The stiff portion is about 14 inches in length. The suture preferably has a non-stiff distal tip, preferably about 1 inch in length, to provide flexibility for passing the suture through bends in the surgical instrument. The remainder of the suture is flexible to facilitate knot tying.

These and other features and advantages of the invention will become apparent from the following detailed description that is provided in connection with the accompanying drawings and illustrated exemplary embodiments of the invention.

DETAILED DESCRIPTION OF THE PREFERRED EMBODIMENT

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The term "endoscopy" encompasses arthroscopy, laparoscopy, hysteroscopy, among others, and endoscopic surgery involves the performance of surgical procedures within a patient's body through small openings as opposed to conventional open surgery through large incisions.

Figure 1:
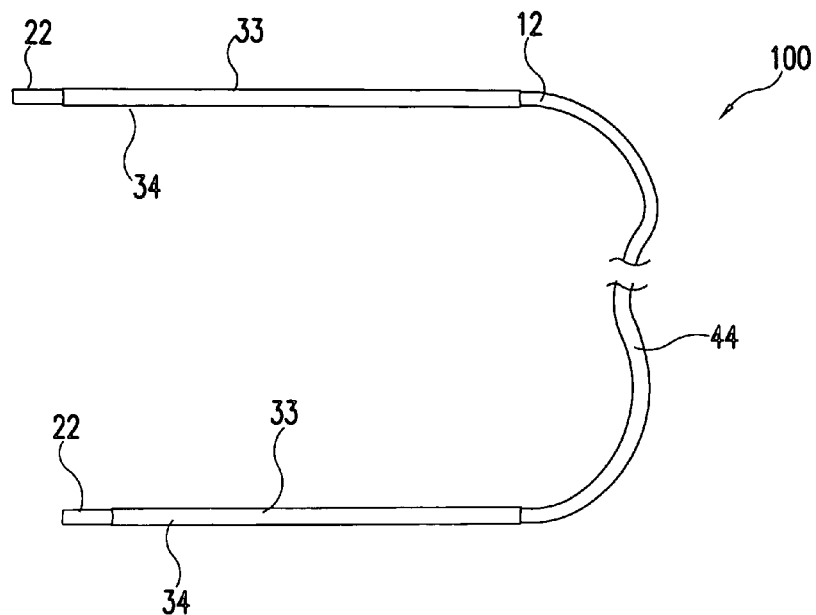
FIG. 1 illustrates a three dimensional view of a stiff tipped suture of the present invention.

Referring now to the drawings, where like elements are designated by like reference numerals, FIG. 1 illustrates a stiff tipped suture 100 of the present invention provided with a stiff portion at its ends to facilitate advancement of the suture ends through a cannulated surgical instrument employed in surgical repairs requiring the passing of sutures to various locations.

In the preferred embodiment, the stiff tipped suture 100 comprises an elongated member 12 formed of a length 44 of conventional (non-stiffened) suture provided with a stiff portion 33 adjacent one or both ends 22. Preferably, the elongated member 12 is a suture formed of a plurality of woven or braided strands or fibers. For the purposes of this application, the term "strand" is used generically, as a strand may be any wire-like material which is sterilizable, flexible and strong enough for the intended applications. Although a multi-stranded member 12 is preferred, the present invention has equal applicability to a stiff tipped suture comprising a single mono-filament strand.

Suture strands within the scope of the invention can be of any type used or contemplated for operative procedures. The suture strands can be synthetic or natural, bioabsorbable or non-absorbable or, as noted above, a monofilament or multi-filament in a braided or twisted form. Examples of absorbable mono-filament sutures include natural sutures such as surgical gut and collagen, and synthetic sutures such as homopolymers and copolymers of p-dioxanone. Examples of absorbable multi-filament sutures include sutures prepared from fiber-forming polymers of one or more lactones, e.g. Vicryl poly(lactide-co-glycolide) multifilament suture. Examples of non-absorbable monofilament and multifilament sutures include nylon, polypropylene, steel, polyvinylidene fluoride, linen, cotton, silk, and polyesters such as polyethylene terephthalate (PET). The suture of the present invention may be a FiberWire suture comprised of ultrahigh molecular weight polypropylene, as described in co-pending U.S. Ser. No. 09/950,598, filed Sep. 13, 2001, the disclosure of which is herein incorporated by reference.

As illustrated in FIG. 1, the distal tip 22 at the end of the stiff tipped suture 100 is flexible and has a length of about 1 inches. The stiff portion 33 adjacent one or both ends preferably has a length of about 14 inches.

The stiff portion 33 of the suture 100 can be made in a number of ways. In a preferred embodiment of the invention, the stiff portion is formed by coating a portion of the suture with cyanoacrylate (sold under the tradenames Krazy Glue® or Super Glue). The stiff portion may also be formed by the application of a wax or polymer coating. Alternatively, the stiffness may be imparted by heat shrink or other heat treating methods.

If the stiff portion is formed of a coating, identified by reference number 34 in FIG. 1, the coating is preferably applied by mounting the suture on a mandrel and dipping the suture in the substance to be coated. Other conventional coating techniques, such as spraying, may also be used. If the suture comprises multi-filament strands, coating 34 preferably fills the interstices between the multi-filament strands forming the elongated body 20 to provide the stiff tipped suture 100 with a firm and stiff yet flexible exterior surface for easy advancement of the suture to a work site, as described in more detail below.

The stiff portion is preferably formed completely to the end of the suture, and, after cutting, the end tip of the suture is then preferably massaged to obtain flexible, non-stiff, tip portion 22. The non-stiff tip portion 22 at the leading end of the suture provides flexibility and allows the suture tip to easily follow the bend of an insertion instrument.

The stiff tipped suture 100 of the present invention, described above with reference to FIG. 1, may be employed in various surgical medical procedures for advancing the suture in the proximity of a surgical site, and for employing the suture with a cannulated instrument during such surgical procedures. For example, the stiff tipped suture 100 may be employed in endoscopic and arthroscopic procedures, including but not limited to arthroscopic rotator cuff repair, Bankhart shoulder repair, meniscal repair, and any orthopaedic procedure that requires tying a knot through soft tissue or bone tunnels, for example, or in conjunction with fixation devices, such as suture anchors. Additionally, the stiff tipped suture 100 may be utilized in other general surgical and specialty procedures that require suturing at a remote site, such as inside the body. The stiff tipped suture of the present invention may be also used in repairs where suture visibility or finger access can be limited.

It will be appreciated, of course, that while the stiff tipped suture 100 may be particularly useful for performing remote procedures through access sheaths, trocars and cannulated surgical instruments, it will also find use in open surgical procedures where its ability to confer a stiff yet flexible suture strand will also provide advantages.

Figure 3:
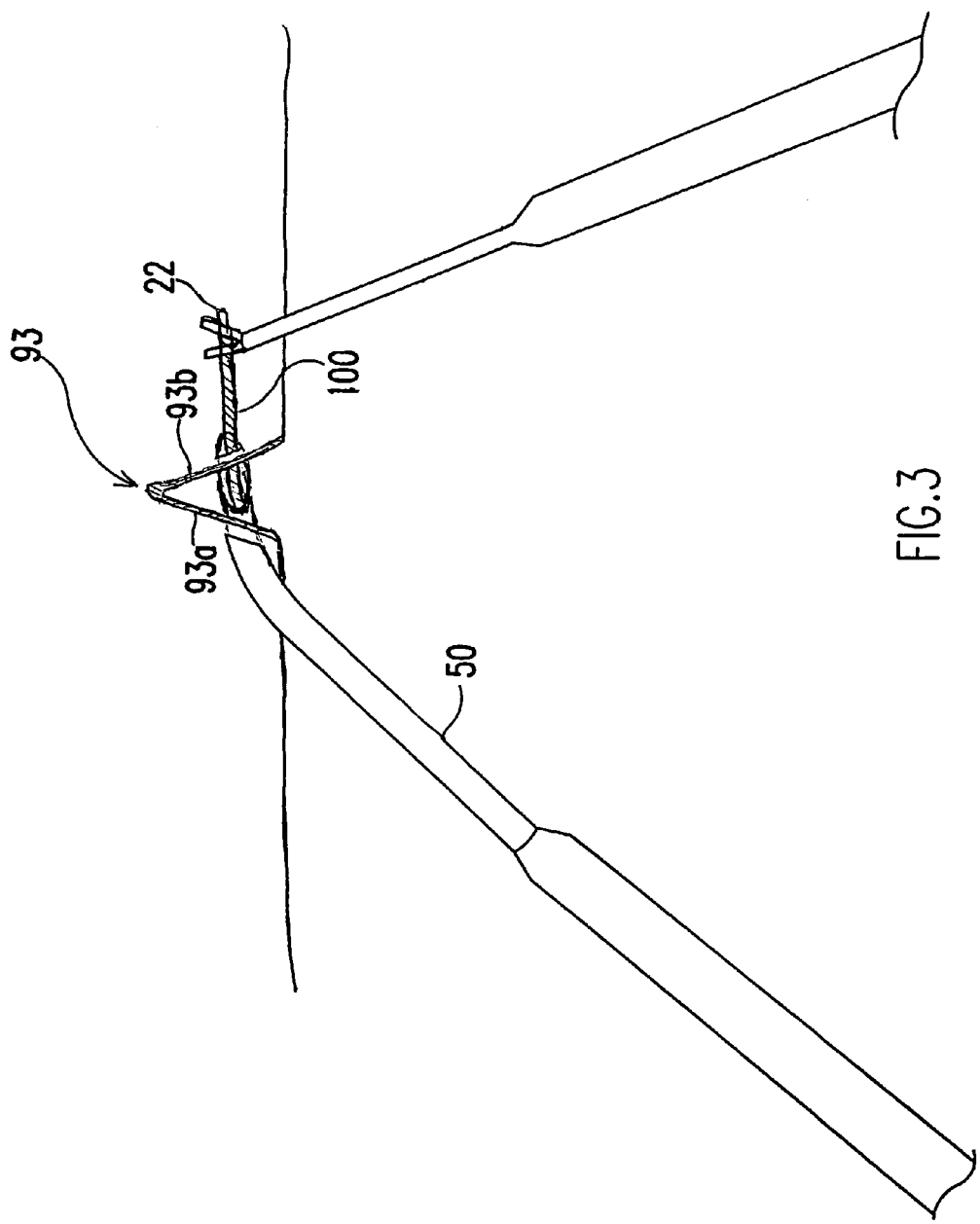
FIG. 3 is a schematic view of a surgical site undergoing a suturing operation according to a method of the present invention.

To better illustrate an exemplary surgical procedure conducted with the stiff tipped suture 100 of the present invention, reference is now made to FIG. 3, which illustrates a schematic view of a surgical site 90 provided with a work site 93, which is typically a torn tissue to be sutured.

Figure 2:
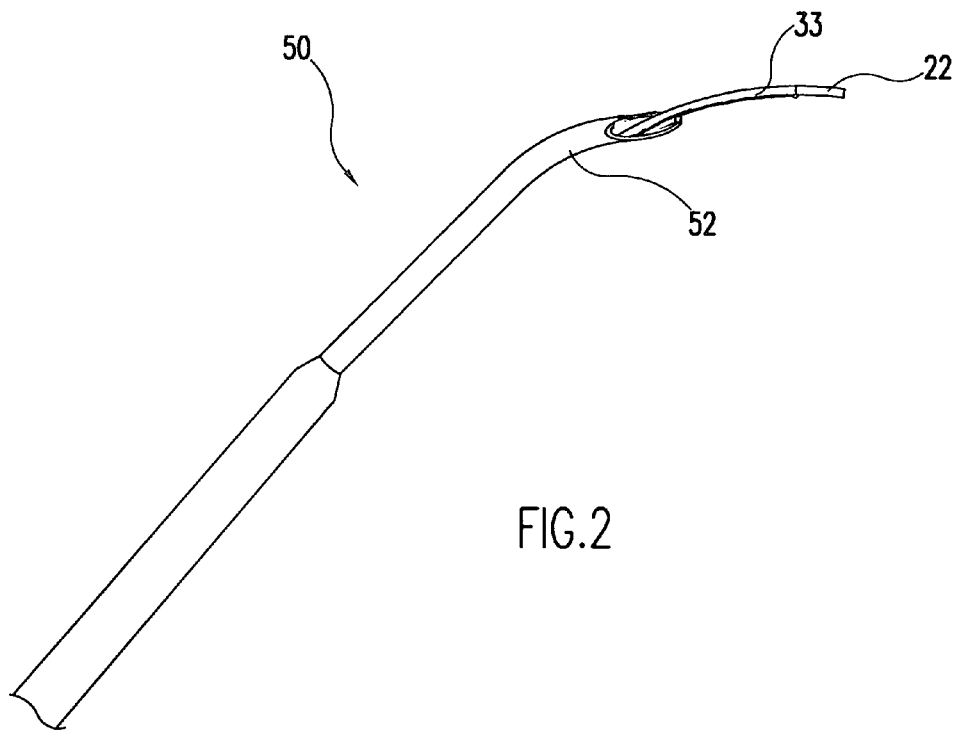
FIG. 2 illustrates a schematic view of a cannulated instrument to be employed with the stiff tipped suture of FIG. 1.

Preferably, the stiff tipped suture 100 of FIG. 1 is employed in conjunction with a cannulated instrument, such as cannulated Suture Lasso instrument 50 of FIGS. 2–3, which is sold by Arthrex, Inc. of Naples, Fla., the assignee of the present application. As detailed in FIG. 2, the cannulated Suture Lasso instrument 50 is provided with a sharp cannulated helical tip 52 that allows a surgeon to pass suture in the low 6 o'clock position from a superior portal by supination of the hand. The curved helical tip 52 of the Suture Lasso instrument 50 is particularly important for challenging angles in cuff repairs, for example, and for accessing soft tissue sites which are either angled or not easily accessible to the surgeon. Since the tip 52 is helical and curved, a braided suture is ordinarily difficult to deploy through the Suture Lasso instrument 50. By providing suture 100 with a stiff coated portion 33, the present invention provides, however, a suture that can easily pass through a cannulated device, particularly through the curved and bent tip of the device. For example, as shown in FIG. 2, the stiff tipped suture 100 of the present invention allows the surgeon to easily push the suture 100 through the cannulated Suture Lasso instrument 50 including its helical tip 52.

Referring now to FIG. 3, the cannulated Suture Lasso instrument 50 loaded with stiff tipped suture 100 is placed in the proximity of the surgical site 93. By hand supination, the sharp cannulated helical tip 52 is pierced through both tissue regions 93a, 93b of the surgical site 93 to be sutured, and the suture is advanced through the instrument. The distal end 22 of the stiff tipped suture 100 extending from the tip of the instrument is then grasped and retrieved from the surgical site 93 through a posterior cannula with a suture retriever instrument, such as the suture retriever described in U.S. Pat. No. 6,074,403 to Nord, the disclosure of which is incorporated by reference herein. In this manner, the stiff tipped suture 100 of the present invention is advanced through tissue regions 93a, 93b of the surgical site 93.

After passing through the tissue regions 93a, 93b to be sutured, the distal end 22 and the coated portion 33 are extracted and cut off At least one knot is subsequently formed, advanced and tightened in the remaining flexible, uncoated suture to secure the tissue together.

Although the embodiment of the present invention has been described above with reference to a specific cannulated instrument, such as the cannulated Suture Lasso instrument 50 of FIGS. 2–3, it must be understood that the invention has equal applicability to other cannulated suturing instruments, such as the suture hook instrument described in U.S. Pat. No. 4,890,615, described earlier, or other endoscopic cannulated instruments of various shapes and geometries for use in various surgical procedures which allow easy passage of stiff tipped sutures of the present invention.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of suturing tissue within a body, comprising the steps of:
    providing a suture strand having an elongated stiff portion at one end adjacent to an elongated non-stiff flexible portion, the elongated stiff portion further including a non-stiff leading tip to facilitate passing of the suture strand through a bend of a cannulated instrument;
    advancing the non-stiff leading tip with the elongated stiff portion through the cannulated instrument, the cannulated instrument being provided with a sharp cannulated tip;
    positioning the cannulated instrument with the non-stiff leading tip and the elongated stiff portion in the proximity of a tissue to be sutured;

penetrating the tissue to be sutured with the sharp tip of the cannulated instrument;

advancing the suture strand through the cannulated instrument so that the non-stiff leading tip is exposed at the cannulated tip of the instrument; and retrieving the suture end having the elongated stiff portion and pulling the non-stiff leading tip and the elongated stiff portion through the tissue to be sutured.

2. The method of claim 1, wherein the suture is a multi-stranded suture.

3. The method of claim 1 further comprising the step of removing the suture end having the elongated stiff portion after retrieving the suture end to leave the flexible, non-stiff portion through the tissue for tying knots.

4. The method of claim 3, further comprising the step of tying a knot in the flexible, non-stiff portion of the suture to secure the tissue together.

* * * * *